United States Patent [19]

Essenfeld

[11] Patent Number: 4,855,520

[45] Date of Patent: Aug. 8, 1989

[54] PROCESS FOR THE PREPARATION OF NAPHTHACENES

[75] Inventor: Amy P. Essenfeld, Stamford, Conn.

[73] Assignee: American Cyanamid Company, Stamford, Conn.

[21] Appl. No.: 80,733

[22] Filed: Aug. 3, 1987

[51] Int. Cl.[4] ................................................ C07C 1/32
[52] U.S. Cl. ...................................... 585/409; 585/26; 585/416; 585/408; 585/469
[58] Field of Search ................. 585/26, 409, 416, 469, 585/408

[56] References Cited

PUBLICATIONS

Moureu et al., C. R. Acad. Sci. (1926), vol. 182, 1440.
Moureu et al., Bull. Soc. Chem. (1930), 216.
Rigaudu et al., Tetrahedron (1977), vol. 33, 767.
Wittig et al., J. Fur Praktische Chemie N. F. (1942), vol. 160, 242.

*Primary Examiner*—Asok Pal
*Attorney, Agent, or Firm*—Frank M. Van Riet

[57] ABSTRACT

A process for the preparation of a substituted naphthacene is disclosed wherein a 1,3-diphenylpropargyl alcohol is reacted with an alkanesulfonyl halide, the resultant reaction product is heated in the presence of a hindered amine base and the resultant substituted naphthacene is recovered.

19 Claims, No Drawings

PROCESS FOR THE PREPARATION OF NAPHTHACENES

BACKGROUND OF THE INVENTION

Substituted naphthacenes are known fluorescers and used extensively in the manufacture of chemiluminescent lighting devices in combination with oxalates and peroxide generators. Rubrene per se has been commercially available for many years and is generally produced by the reaction of 1,1,3-triphenylpropargyl alcohol and thionyl chloride with subsequent heating of the resultant reaction product in the presence of an amine base. Ofttimes, the rubrene is produced in the form of its sulfonate by reaction with fuming sulfuric acid. Yields of rubrene utilizing the above procedure, however, are relatively low, i.e., 30–50% and not very reproducible.

Other procedures for the production of rubrene are taught in Moureu et al; C.R. Acad. Sci. (1926), 182, 1440; Moureu et al; Bull. Soc. Chem. (1930), 216, Wittig et al; Journal fur praktische Chemie N.F. (1942), 160, 242; Rigaudy et al; Tetrahedron (1977), 33, 767. In each of the procedures set forth above, the yields range from 20–50% and ofttimes require the isolation and purification of intermediates.

Thus, the industry is always searching for new procedures which enable the recovery of naphthacenes in increased yields and without the need for intermediate isolation and purification.

DESCRIPTION OF THE INVENTION INCLUDING PREFERRED EMBODIMENTS

The present invention provides a process for the preparation of substituted maphthacenes which comprises (1) reaction a solvent solution of a 1,3,-diphenyl-propargyl alcohol, in the presence of an acid scavenger, with an alkanesulfonyl halide at a temperature ranging from about −30° C. to about 30° C. for from about 15 minutes to about 3 hours, (2) heating the reaction product resulting from step (1) to a temperature of from about 70° C. to about reflux for from about 2 to about 8 hours, in an oxygen-free atmosphere, in the absence of light and in the presence of an hindered amine base and (3) recovering the resultant substituted naphthacene.

Step (1) may be conducted utilizing any material which is a solvent for the solid 1,3-diphenylpropargyl alcohol and the alkanesulfonyl halide and has a boiling point above the temperature at which step (1) is conducted. Suitable solvents include methylene chloride, toluene, xylene mixtures, dimethylformamide and the like. While it is possible to use the same solvent in Step (1) which is to be used in Step (2), such is not preferred, since it has been found that higher yields of the naphthacene are achieved when two different solvents are used and furthermore, the recovered naphthacene has a greater purity.

The 1,3-diphenylpropargyl alcohol and alkane sulfonyl halide are preferably reacted in equimolar amounts, however, a slight excess of the halide is tolerable. Higher or lower concentrations of either reactant either result in lower yields of the intermediate or do not enhance the reaction in any significant way.

The acid scavenger employed may be any material which is known to be useful for this purpose. Suitable scavengers are the amines such as triethylamine, pyridine, 1,8-diazabicyclo[5.4.0] undeca-7-ene and the like. Diisopropylethylamine, tetramethylethylenediamine etc. may also be used. Sufficient scavenger should be used to take up substantially all of the acid liberated by the reaction since the presence of an acid media interferes with the naphthacene production since the intermediates are acid sensitive.

The reaction of step (1) is conducted at a temperature of from about −30° C. to about 30° C., preferably from about −10° C. to about 10° C., with agitation, for from about 15 minutes to about 5 hours, preferably from about 1 to about 3 hours.

Once the intermediate is formed, step (2) is commenced by first removing the reaction from the light such as by isolating the reaction vessel in the dark or using a light impermeable reaction vessel ab initio. Once light is removed from the reaction media, the media is heated to a temperature ranging from about 70° C. to reflux (i.e. depending upon the solvent being employed), preferably from about 90° C. to about 120° C.. The heating is continued for from about 2 to about 8 hours, preferably from about 4 to about 6 hours. The reaction media in step (2) is maintained under oxygen-free conditions by feeding nitrogen gas or other equivalent material into the reaction vessel. Sufficient solvent should be retained in the reaction media containing the intermediate to create approximately a 0.5–3.0M solution. Sufficient amounts of hindered amine base are added, preferably dropwise, to pull off protons from the step (1) intermediate and cause cyclization thereof to the naphthacene structure. Suitable hindered amine bases include tertiary amines such as pyridine; substituted pyridines such as 2,4,6-trimethylpyridine; quinoline; N,N-dimethylaniline and the like.

When the solvent employed in step (1) is different than that which is to be used in Step (2) it will be necessary to volatilize off said step (1) solvent between step (1) and step (2) and replace said volatilized solvent with a second solvent. This can be accomplished rather simply by the use of, for example, a Dean-Stark trap. Suitable solvents which may be used in Step (2) include xylenes, toluenes, mixtures thereof, dimethylformamide, and the like.

Recovery of the naphthacene product can be accomplished utilizing any technique known in the art, e.g. filtration, however, purification after recovery is generally conducted, for example, as is shown in U.S. Pat. No. 3888784, hereby incorporated herein by reference. Generally, recovery is accomplished by filtering the step (2) reaction product through a filter such as a sintered glass funnel using an aspirator. Xylenes or other solvent may be used to remove all solids from the reaction vessel and the crude product may be washed, as required, with methanol until the final filtrate is substantially colorless. The final product naphthacene, is colored, i.e., rubrene per se is orange, and is dried to remove all traces of solvent.

The naphthacene products produced by the process of the present invention have the following structure:

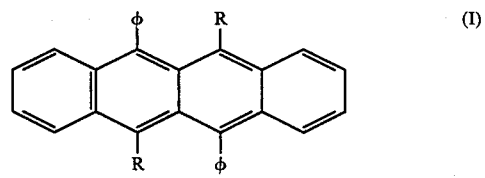

(I)

wherein φ is phenyl and R is hydrogen, phenyl or substituted phenyl, said substituents being alkyl ($C_1$–$C_4$), halogen, cyano, nitro, alkoxy ($C_1$–$C_4$) groups and the like.

The reaction proceeds according to the equation:

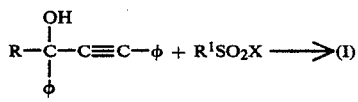

$$R-\underset{\phi}{\underset{|}{C}}-C\equiv C-\phi + R^1SO_2X \longrightarrow (I)$$

wherein R and $\phi$ are as set forth above, $R^1$ is alkyl ($C_1$–$C_4$) and X is a halide, e.g., chloride, fluoride, iodide, etc.

The following examples are set forth for purposes of illustration only and are not to be construed as limitations on the present invention except as set forth in the appended claims. All parts and percentages are by weight unless otherwise specified.

EXAMPLE 1

To a suitable reaction vessel equipped with a mechanical stirrer, addition funnel, Dean-Stark trap, condenser, thermometer with adapter, Claisen adapter and nitrogen inlet are charged 533.8 parts of 1,1,3-triphenylpropargyl alcohol and 1060 parts of methylene chloride. The vessel is stirred until all the alcohol is in solution. The solution is pale yellow. The vessel is cooled and 189.8 parts of triethylamine are slowly added while cooling. 215.2 Parts of methanesulfonyl chloride are charged dropwise while maintaining the temperature at 0°–5° C.. The resultant reaction media is stirred at 0°–5° C. for one hour and then allowed to warm to room temperature and is then stirred for an additional hour. The reaction vessel is then placed in the dark and the contents heated to drive off the methylene chloride which is collected in the Dean-Stark trap. When 331.2 parts are collected, 215 parts of a commercially available xylene mixture is added. 331.2 More parts of methylene chloride are collected and replaced by 215 parts of said xylene mixture during which the reaction media is about 50° C..

To this reaction media are then added, dropwise, 227.4 parts of 2,4,6-trimethylpyridine while the remaining methylene chloride is collected and replaced by 215 parts of the xylene mixture. The temperature is maintained at 95° C. for 6 hours after which the media is cooled to room temperature (30–45 minutes). The resultant reaction media is very thick with solids and is dark red in color. The reaction media is filtered through a sintered glass funnel using an aspirator. Any solids remaining in the reaction vessel are removed by rinsing the vessel several times with xylene. The filtrate is very dark. The crude product is washed nine times with 197.8 part portions of methanol. The final filtrate is colorless. The final product, rubrene, is orange. It is dried overnight to remove traces of methanol. 305 Parts are recovered resulting in a yield of 61%.

EXAMPLE 2

A reaction vessel equipped with a condenser, mechanical stirrer, thermometer, nitrogen purge, Claisen adapter, addition funnel, and Dean-Stark trap is charged with 10.7 parts of 1,1,3-triphenylpropargyl alcohol and 26.5 parts of methylene chloride. The mixture is stirred until all the solid has dissolved. The solution is pale yellow in color. The reaction vessel is cooled to 0-5° C. and then 3.8 parts of triethylamine are slowly added. While maintaining the temperature at 0°–5° C., 4.8 parts of ethanesulfonyl chloride are added dropwise. The resultant reaction mixture is stirred at 0°–5° C. for one hour. The reaction mixture is then warmed to room temperature and stirred for an additional hour at room temperature. The vessel is then protected from light and the contents are heated to distill off the methylene chloride. When 13.2 parts of methylene chloride have been collected, 8.5 parts of a xylene mixture are added along with 4.55 parts of 2,4,6-trimethylpyridine which are added dropwise. When the remaining methylene chloride is collected, 8.7 parts of a xylene mixture are added to the reaction vessel. The temperature is maintained at 100° C. for five hours after which it is cooled to room temperature. The resultant reaction mixture is very thick with solids and is dark red in color. The mixture is filtered through a sintered glass funnel using an aspirator. Any solids remaining in the reaction vessel are rinsed out with a xylene mixture. The filtrate is dark red in color. The crude product is washed five times with 15.8 parts of methanol. The final filtrate is colorless. The final product, rubrene, is an orange solid. The purified product is dried under vacuum overnight to remove any traces of methanol. 3.7 Parts of rubrene are recovered resulting in a yield of 37%.

EXAMPLES 3-5

Following the procedure of Example 1, except as indicated, various alcohols are reacted with various halides to produce substituted naphthacenes. All substituent designations are as set forth above. The results are set forth in Table I, below.

TABLE I

| Ex. No. | Alcohol R | Halide $R^1$ | X | Naphthacene R |
|---|---|---|---|---|
| 3 | hydrogen | methane | chloride | hydrogen |
| 4 | p-chlorophenyl | methane | bromide | p-chlorophenyl |
| 5 | p-methoxyphenyl | ethane | chloride | p-methoxyphenyl |

We claim:

1. A method for the preparation of a naphthacene which comprises (1) reacting a solvent solution of a 1,3-diphenylpropargyl alcohol, in the presence of an acid scavenger, with an alkanesulfonyl halide at a temperature of from about −30° C. to about 30° C. for from about 15 minutes to about 3 hours, (2) heating the resultant reaction product to a temperature of from about 70° C. to about reflux from about 2 to about 8 hours, in an oxygen-free atmosphere, in the absence of light and in the presence of a hindered amine base and (3) recovering the resultant naphthacene.

2. A method according to claim 1 wherein said acid scavenger is an amine.

3. A method according to claim 2 wherein said amine is triethylamine.

4. A method according to claim 1 wherein said hindered amine base is 2,4,6-trimethylpyridine.

5. A method according to claim 2 wherein said hindered amine base is 2,4,6-trimethylpyridine.

6. A method according to claim 1 wherein the said solvent in step (1) is methylene chloride and the solvent in step (2) is a xylene mixture.

7. A method according to claim 6 wherein said acid scavenger is an amine.

8. A method according to claim 7 wherein said amine is triethylamine.

9. A method according to claim 6 wherein said hindered amine base is 2,4,6-trimethylpyridine.

10. A method according to claim 7 wherein said hindered amine base is 2,4,6-trimethylpyridine.

11. A method according to claim 8 wherein said hindered amine base is 2,4,6-trimethylpyridine.

12. A method according to claim 1 wherein said oxygen-free atmosphere is provided by nitrogen gas.

13. A method according to claim 1 wherein said alcohol is 1,1,3-triphenylpropargyl alcohol.

14. A method according to claim 1 wherein said alkanesulfonyl halide is methanesulfonyl chloride.

15. A method according to claim 1 wherein said alcohol is 1,1,3-triphenylpropargyl alcohol and said alkanesulfonyl halide is methanesulfonyl chloride.

16. A method according to claim 15 wherein said acid scavenger is an amine.

17. A method according to claim 16 wherein said amine is triethylamine.

18. A method according to claim 15 wherein said hindered amine base is 2,4,6-trimethylpyridine.

19. A method according to claim 15 wherein said solvent in step (1) is methylene chloride and the solvent is step (2) is a xylene mixture.

* * * * *